United States Patent
Kingsley

(10) Patent No.: US 9,259,346 B2
(45) Date of Patent: Feb. 16, 2016

(54) METHOD FOR OPERATING A THERAPEUTIC COOLING APPARATUS

(76) Inventor: Kyle E Kingsley, Minneapolis, MN (US)

(*) Notice: Subject to any disclaimer, the term of this patent is extended or adjusted under 35 U.S.C. 154(b) by 1132 days.

(21) Appl. No.: 13/208,334

(22) Filed: Aug. 11, 2011

(65) Prior Publication Data

US 2013/0041437 A1 Feb. 14, 2013

Related U.S. Application Data

(63) Continuation-in-part of application No. 13/208,324, filed on Aug. 11, 2011, now abandoned.

(51) Int. Cl.
*A61F 7/00* (2006.01)
*A61F 7/10* (2006.01)

(52) U.S. Cl.
CPC ........... *A61F 7/00* (2013.01); *A61F 2007/0008* (2013.01); *A61F 2007/0029* (2013.01); *A61F 2007/0031* (2013.01); *A61F 2007/0034* (2013.01); *A61F 2007/0043* (2013.01); *A61F 2007/0045* (2013.01); *A61F 2007/0063* (2013.01); *A61F 2007/0096* (2013.01); *A61F 2007/108* (2013.01)

(58) Field of Classification Search
CPC .............. A61F 7/00; A61F 2007/0002; A61F 2007/0008; A61F 2007/0009
USPC .................................................. 607/108, 109
See application file for complete search history.

(56) References Cited

U.S. PATENT DOCUMENTS

| | | | |
|---|---|---|---|
| 2,702,552 A * | 2/1955 | Moodie | 607/114 |
| 3,378,004 A | 4/1968 | Claycomb et al. | |
| 4,845,338 A | 7/1989 | Lakic | |
| 4,920,963 A * | 5/1990 | Brader | 607/109 |
| 5,241,958 A * | 9/1993 | Noeldner | 607/86 |
| 5,277,695 A | 1/1994 | Johnson, Jr. et al. | |
| 5,292,347 A * | 3/1994 | Pompei | 607/104 |
| 5,383,918 A * | 1/1995 | Panetta | 607/104 |
| 6,245,094 B1 * | 6/2001 | Pompei | 607/104 |
| 6,416,532 B1 * | 7/2002 | Fallik | 607/109 |
| 6,461,379 B1 * | 10/2002 | Carson et al. | 607/104 |
| 6,565,593 B2 * | 5/2003 | Diana | 607/108 |
| 6,962,600 B2 * | 11/2005 | Lennox et al. | 607/104 |
| 7,008,445 B2 * | 3/2006 | Lennox | 607/109 |
| 7,052,509 B2 * | 5/2006 | Lennox et al. | 607/109 |
| 7,547,320 B2 * | 6/2009 | Schook et al. | 607/104 |
| 7,621,945 B2 * | 11/2009 | Lennox et al. | 607/109 |
| 7,640,764 B2 * | 1/2010 | Gammons et al. | 62/259.3 |
| 7,771,461 B2 * | 8/2010 | Schock et al. | 607/108 |

(Continued)

*Primary Examiner* — Kaitlyn Smith
(74) *Attorney, Agent, or Firm* — Hamre, Schumann, Mueller & Larson, P.C.

(57) ABSTRACT

A method comprises preparing a cooling device for use in a therapeutic cooling apparatus. The cooling device comprises a self-contained unit. The therapeutic cooling apparatus comprises a cavity being configured to accept a portion of a user's body part, a quantity of a liquid for surrounding the body part and an apparatus portion being configured to retain the cooling device. The apparatus portion further comprises a divider separating the apparatus portion from the cavity. The divider is configured to be operable for transferring heat from the liquid to the cooling device. The method further comprises chilling the cooling device, placing the body part into the cavity, and filling the cavity with the liquid to surround the body part enabling a heat transfer from the body part to the liquid and a heat transfer from the liquid through the divider to the cooling device to cool the user.

7 Claims, 13 Drawing Sheets

(56) References Cited

U.S. PATENT DOCUMENTS

| | | |
|---|---|---|
| 7,806,841 B2 | 10/2010 | Caselnova |
| 8,425,582 B2 * | 4/2013 | Schock et al. ........ 607/108 |
| 8,435,277 B2 * | 5/2013 | Schock et al. ........ 607/104 |
| 8,449,590 B2 * | 5/2013 | Brader ............... 607/110 |
| 8,454,671 B2 * | 6/2013 | Lennox et al. ........ 607/104 |
| 8,529,613 B2 * | 9/2013 | Radziunas et al. ..... 607/110 |
| 2002/0161419 A1 * | 10/2002 | Carson et al. ........ 607/104 |
| 2003/0089370 A1 * | 5/2003 | Daffer et al. ........ 128/201.24 |
| 2004/0127964 A1 * | 7/2004 | Grahn et al. ......... 607/108 |
| 2004/0158303 A1 * | 8/2004 | Lennox et al. ........ 607/109 |
| 2004/0225341 A1 * | 11/2004 | Schock et al. ........ 607/104 |
| 2004/0243202 A1 * | 12/2004 | Lennox .............. 607/104 |
| 2004/0260369 A1 * | 12/2004 | Schock et al. ........ 607/104 |
| 2006/0030915 A1 * | 2/2006 | Lennox et al. ........ 607/104 |
| 2006/0030916 A1 * | 2/2006 | Lennox .............. 607/104 |
| 2006/0058858 A1 | 3/2006 | Smith |
| 2006/0069418 A1 * | 3/2006 | Schock et al. ........ 607/104 |
| 2006/0107950 A1 * | 5/2006 | Hutchinson ......... 128/201.22 |
| 2006/0111766 A1 * | 5/2006 | Grahn et al. ......... 607/104 |
| 2006/0282140 A1 * | 12/2006 | Schock et al. ........ 607/108 |
| 2006/0282141 A1 * | 12/2006 | Schock et al. ........ 607/108 |
| 2006/0282142 A1 * | 12/2006 | Schock et al. ........ 607/108 |
| 2006/0287697 A1 * | 12/2006 | Lennox .............. 607/96 |
| 2007/0100264 A1 | 5/2007 | Hanson |
| 2007/0106351 A1 * | 5/2007 | Ferguson et al. ...... 607/109 |
| 2008/0269852 A1 * | 10/2008 | Lennox et al. ........ 607/104 |
| 2009/0157153 A1 * | 6/2009 | Lemke et al. ......... 607/114 |
| 2009/0276018 A1 * | 11/2009 | Brader .............. 607/104 |
| 2010/0324635 A1 * | 12/2010 | Kreck ............... 607/105 |
| 2011/0041779 A1 | 2/2011 | Hurwitz |
| 2012/0310312 A1 * | 12/2012 | Yee ................. 607/105 |
| 2013/0041439 A1 * | 2/2013 | Gallagher ........... 607/109 |
| 2013/0041440 A1 * | 2/2013 | Kingsley ............ 607/109 |
| 2013/0116761 A1 * | 5/2013 | Kreck ............... 607/105 |

* cited by examiner

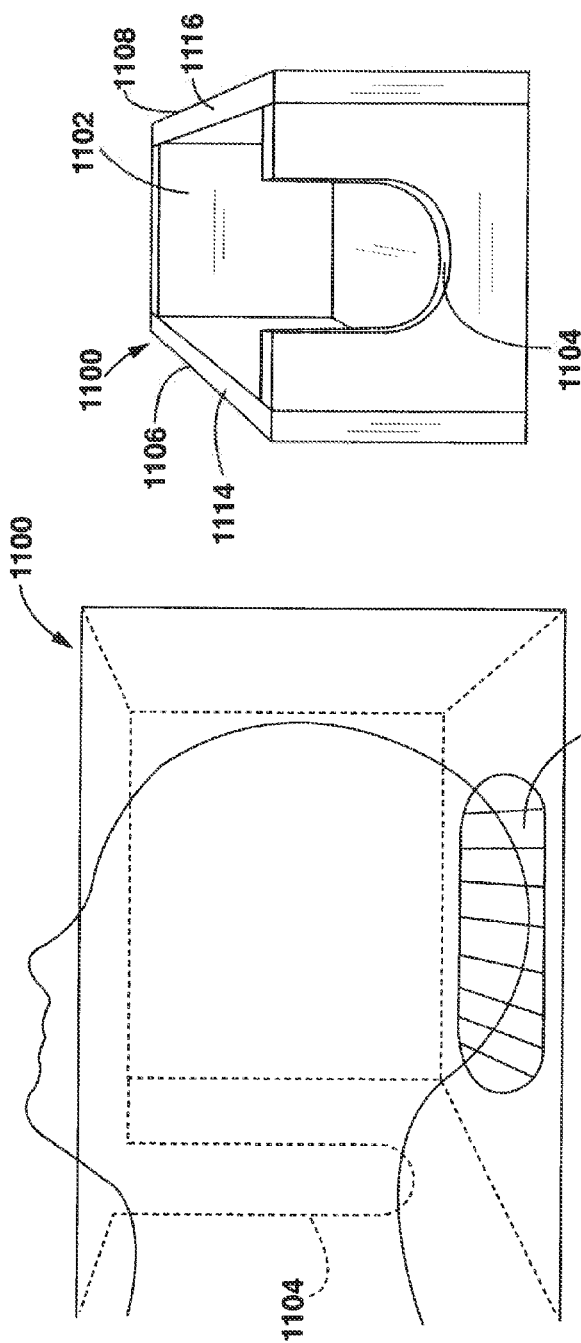
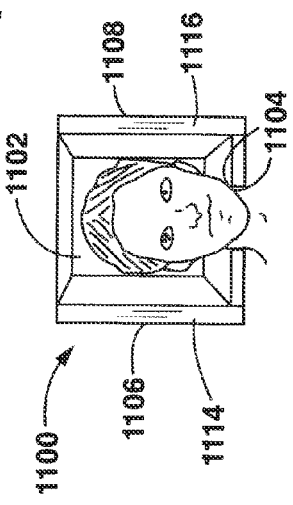
FIG. 11A
FIG. 11B
FIG. 11C

METHOD FOR OPERATING A THERAPEUTIC COOLING APPARATUS

CROSS-REFERENCE TO RELATED APPLICATIONS

The present continuation-in-part patent application claims priority benefit under 35 U.S.C. 120 of the U.S. nonprovisional patent application Ser. No. 13/208,324, filed 11 Aug. 2011 now abandoned and titled "Apparatus for Therapeutic Cooling", which is hereby incorporated by reference for all purposes to the extent that such subject matter is not inconsistent herewith or limiting hereof.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office, patent file or records, but otherwise reserves all copyright rights whatsoever.

FIELD OF THE INVENTION

One or more embodiments of the invention generally relate to therapeutic devices. More particularly, the invention relates to devices for therapeutic cooling.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, another aspect of the prior art generally useful to be aware of is that application of cold or heat therapy to an extremity, often a leg, is frequently performed for injury treatment and prevention in athletes. Acute and chronic injuries/diseases of the lower and upper extremities are common and are frequently treated with the application of cold therapy to the affected area. This may be performed frequently for the injured and healthy athlete alike. Many runners, for example, choose to apply cold via ice bags or other devices to their legs after long runs or may even take a lower body ice bath. Athletes with acute injuries such as cartilage, ligament, tendon, muscle or even bone injuries may choose to apply cold therapy to the injured area many times in a single day.

Common approaches for therapy include application of ice directly with ice in hand and massaging of area with ice, application of ice bags, submersion in ice baths or application of cooling packs or material to the affected area either using the hand or held directly to the affected area of the body directly by another device. Other approaches include cooling devices that require attachment to a refrigeration device or have cables/tubes extending out of the device.

Athletes, in events such as the triathlon, often submerge their entire lower body in a lake or other body of water following a race. Some athletes, particularly in endurance events perform a lower extremity ice bath in a bath tub or trash can immediately following events or training. Ice packs are often applied following injury to the lower extremity in events such as football or other many other sports.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which:

FIGS. 11A-C illustrates an example therapeutic device, in accordance with an embodiment of the present invention;

Figure 1:
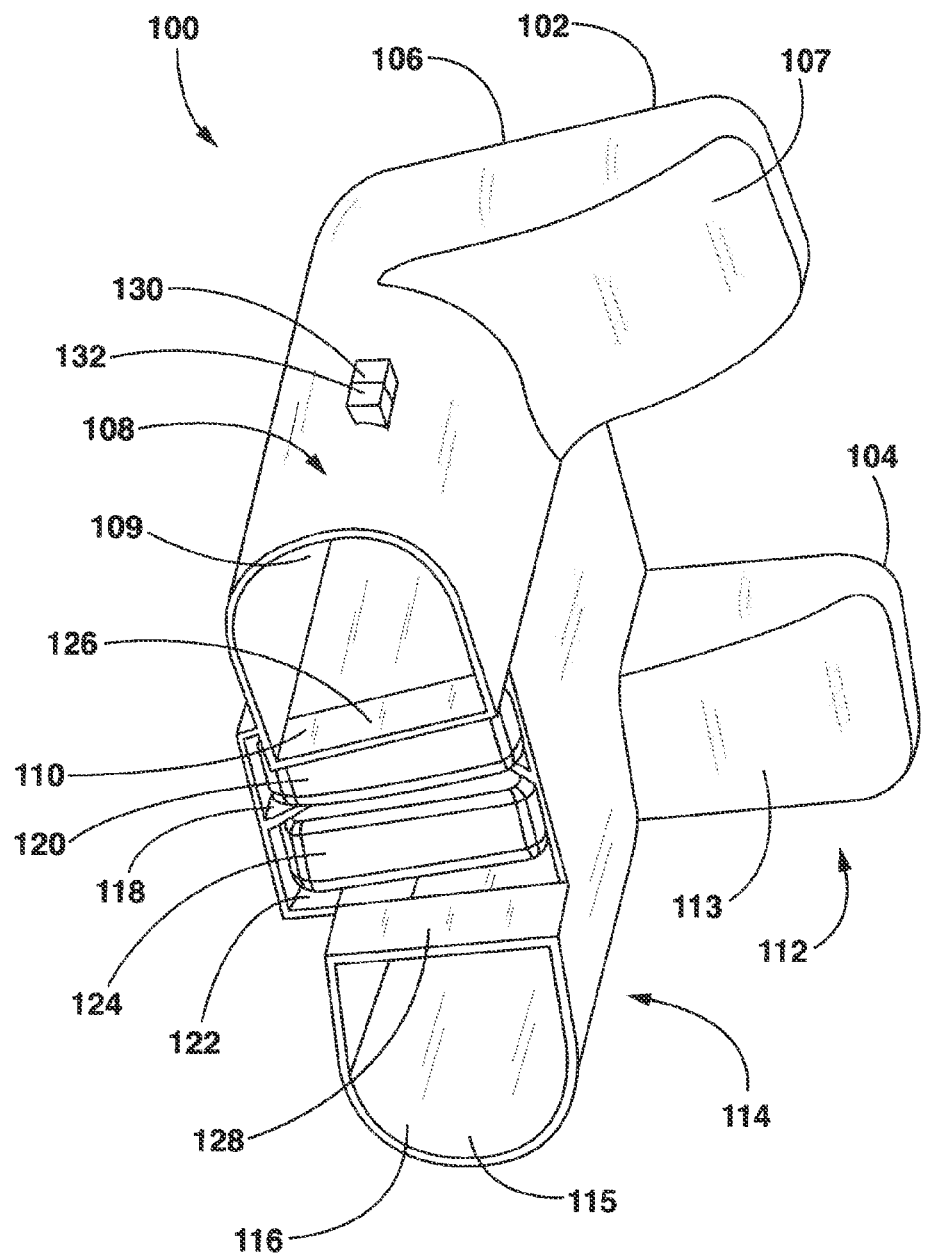
FIG. 1 illustrates an example therapeutic device, in accordance with an embodiment of the present invention.

Unless otherwise indicated illustrations in the figures are not necessarily drawn to scale.

DETAILED DESCRIPTION OF THE PREFERRED EMBODIMENTS

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present application or of any further application derived therefrom.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

Embodiments of the present invention will be described for providing therapeutic devices for performing therapeutic treatments.

FIG. 1 illustrates an example therapeutic device, in accordance with an embodiment of the present invention.

A therapeutic device 100 includes a left portion 102 and a right portion 104.

Therapeutic device 100 receives limbs (not shown) of a person (not shown) for the purpose of cooling the limb in order to provide therapeutic treatment.

Left portion 102 receives a left limb of a person and right portion 104 receives a right limb of a person.

Left portion 102 includes a base portion 106 and an upper portion 108.

Base portion 106 provides a cavity 107 for receiving the left foot (not shown) of a person receiving therapeutic treatment.

Upper portion 108 provides a cavity 109 for receiving the left leg (not shown) of a person receiving therapeutic treatment.

Entry of limb into left portion 102 is enabled via an opening 110.

Right portion 104 includes a base portion 112 and an upper portion 114.

Base portion 112 provides a cavity 113 for receiving the right foot (not shown) of a person receiving therapeutic treatment.

Upper portion 114 provides a cavity 115 for receiving the right leg (not shown) of a person receiving therapeutic treatment.

Entry of limb into right portion 104 is enabled via an opening 116.

Left portion 102 includes a receptacle 118 for receiving a cooling device 120 and right portion 104 includes a receptacle 122 for receiving a cooling device 124. Other embodiments may include only a single receptacle between left portion 102 and right portion 104.

A divider 126 provides separation between receptacle 118 and cavity 109.

A divider 128 provides separation between receptacle 122 and cavity 115.

A temperature measuring device 130 may be joined to therapeutic device 100. Temperature measuring device may comprise a digital or analog thermometer or other temperature indicators such as color-changing, temperature sensitive tape adherent to the therapeutic device, etc. Temperature measuring device 130 may be joined to therapeutic device 100 at various locations, preferably where the user and/or person assisting the user may easily observe. Some embodiments may not include temperature measuring device 130.

A small pump device 132 may be employed for circulation of the liquid in the chamber that contains the limbs for therapeutic treatment. Pump device 132 may be combined with temperature measuring device 100. In some embodiments pump device 132 may be separate from temperature measuring device 130 and may be located at a different location. Some embodiment may not include pump device 132.

In operation, cooling device 120 and cooling device 124 provide cooling to liquid (not shown) located within therapeutic device 100. Furthermore, cooled liquid provides cooling to limbs of person inserted into therapeutic device 100 for providing therapeutic treatment.

Figure 2A:
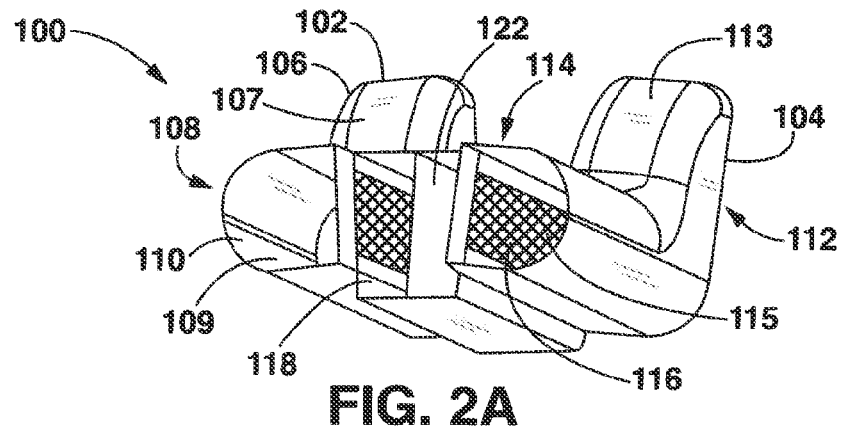
FIGS. 2A-C further illustrate the example therapeutic device as described with reference to FIG. 1, in accordance with an embodiment of the present invention.
Figure 2B:
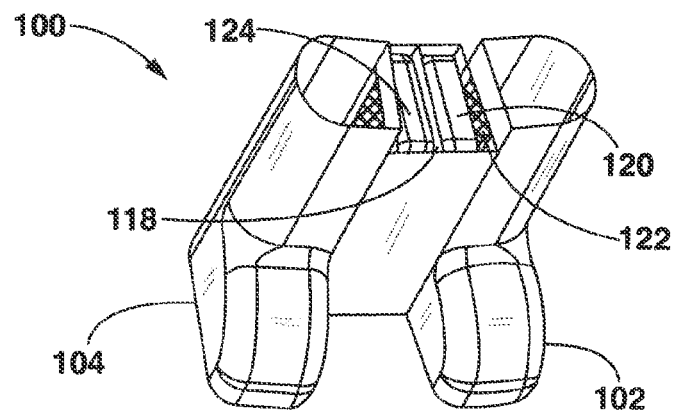
Figure 2C:
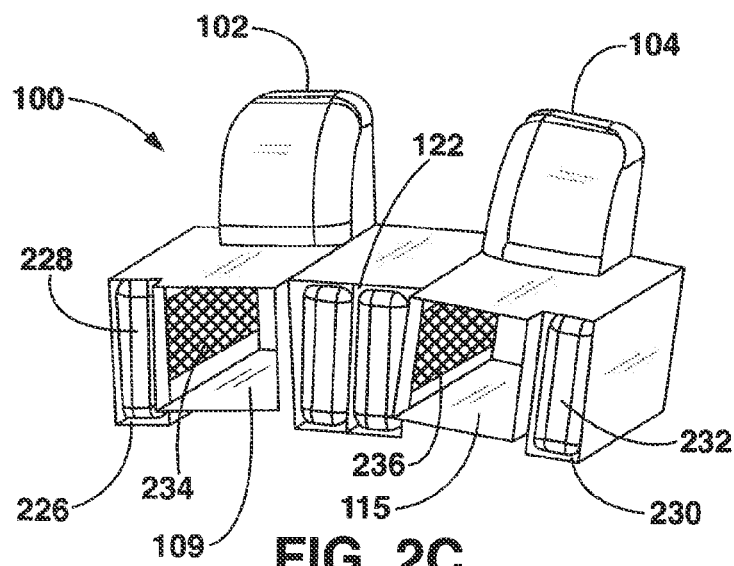

FIGS. 2A-C further illustrate the example therapeutic device as described with reference to FIG. 1, in accordance with an embodiment of the present invention.

FIG. 2A illustrates therapeutic device 100 without insertion of cooling device 120 and cooling device 124 as described with reference to FIG. 1.

FIG. 2B presents front view of example therapeutic device 100 as described with reference to FIG. 1 with cooling device 120 and cooling device 124 inserted into therapeutic device 100.

FIG. 2C illustrates example therapeutic device 100 with inclusion of a receptacle 226 associated with a cooling device 228 and receptacle 230 associated with a cooling device 232.

Receptacle 226 with cooling device 228 and receptacle 230 with cooling device 232 provide additional cooling capabilities to the capabilities as described with reference to FIG. 1.

Dividers separate receptacles and cavities. As an example, a divider 234 separates receptacle 226 from cavity 109 and a divider 236 separates receptacle 122 from cavity 115.

Figure 3:
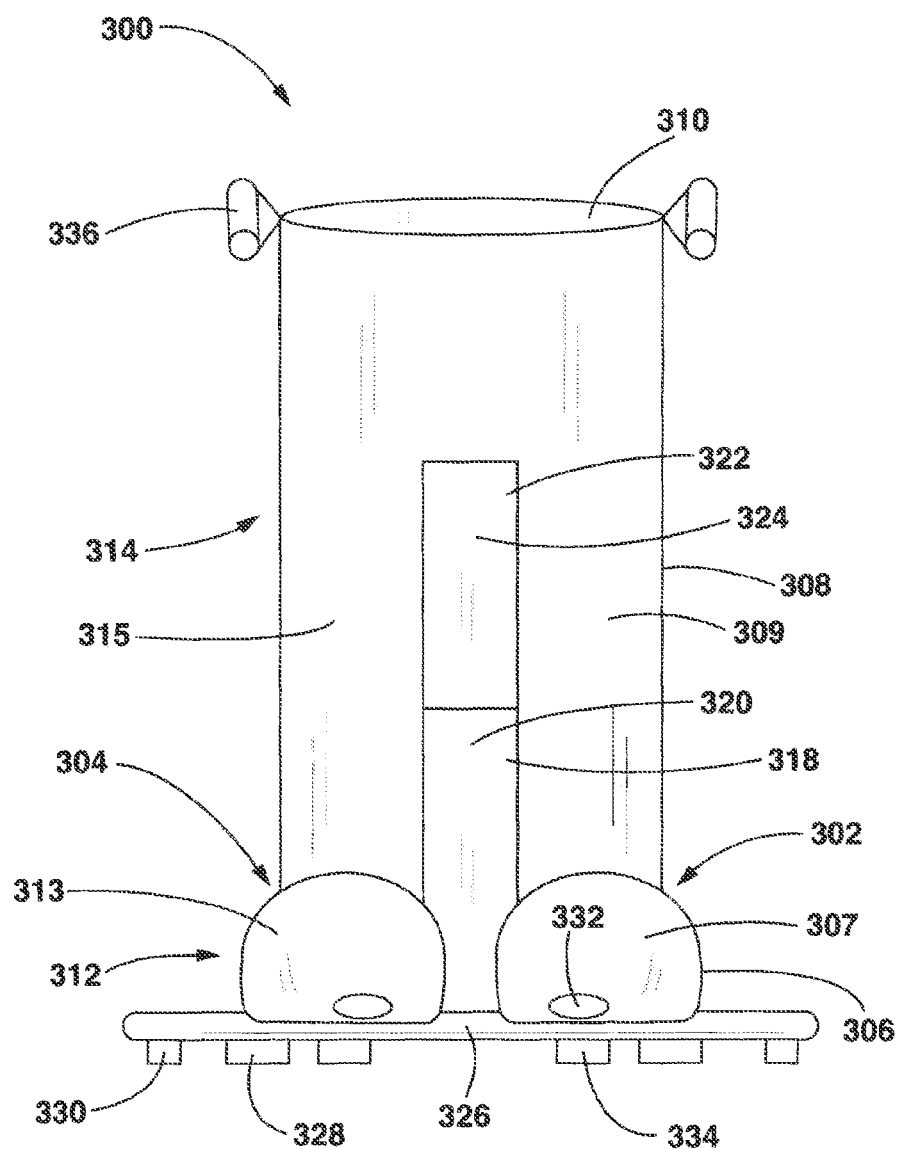
FIG. 3 illustrates an example therapeutic device, in accordance with an embodiment of the present invention.

FIG. 3 illustrates an example therapeutic device, in accordance with an embodiment of the present invention.

A therapeutic device 300 includes a left portion 302 and a right portion 304.

Therapeutic device 300 receives body portions (not shown) of a person (not shown) for the purpose of cooling the body portions in order to provide therapeutic treatment.

Left portion 302 receives a left limb of a person and right portion 304 receives a right limb of a person.

Left portion 302 includes a base portion 306 and an upper portion 308.

Base portion 306 provides a cavity 307 for receiving the left foot (not shown) of a person receiving therapeutic treatment.

Upper portion 308 provides a cavity 309 for receiving the left leg (not shown) of a person receiving therapeutic treatment.

Entry of body portions is enabled via an opening 310.

Right portion 304 includes a base portion 312 and an upper portion 314.

Base portion 312 provides a cavity 313 for receiving the right foot (not shown) of a person receiving therapeutic treatment.

Upper portion 314 provides a cavity 315 for receiving the right leg (not shown) of a person receiving therapeutic treatment.

A receptacle 318 for receiving a cooling device 320 is located between upper portion 308 and upper portion 314.

A receptacle 322 for receiving a cooling device 324 is located above receptacle 318 and between upper portion 308 and upper portion 314.

A base 326 provides for increased support and stability.

A multiplicity of wheels, with a sampling denoted as a wheel 328, provide for ease of movement.

A multiplicity of adherent devices, with a sampling denoted as an adherent device 330, provides for traction and reduced movement of therapeutic device 300.

A multiplicity of drains, with a sampling denoted as a drain 332, and a multiplicity of sealing devices, with a sampling denoted as a sealing device 334, provide for retaining and expelling liquid from therapeutic device 300.

Supports/grips for arms 336 may provide additional stability/comfort. Supports/grips for arms 336 may provide a platform on which the individual could lean onto with arms for support.

In operation, cooling device 320 and cooling device 324 provide cooling to liquid (not shown) located within therapeutic device 300. Furthermore, cooled liquid provides cooling to limbs of person inserted into therapeutic device 300 for providing therapeutic treatment.

Figure 4:
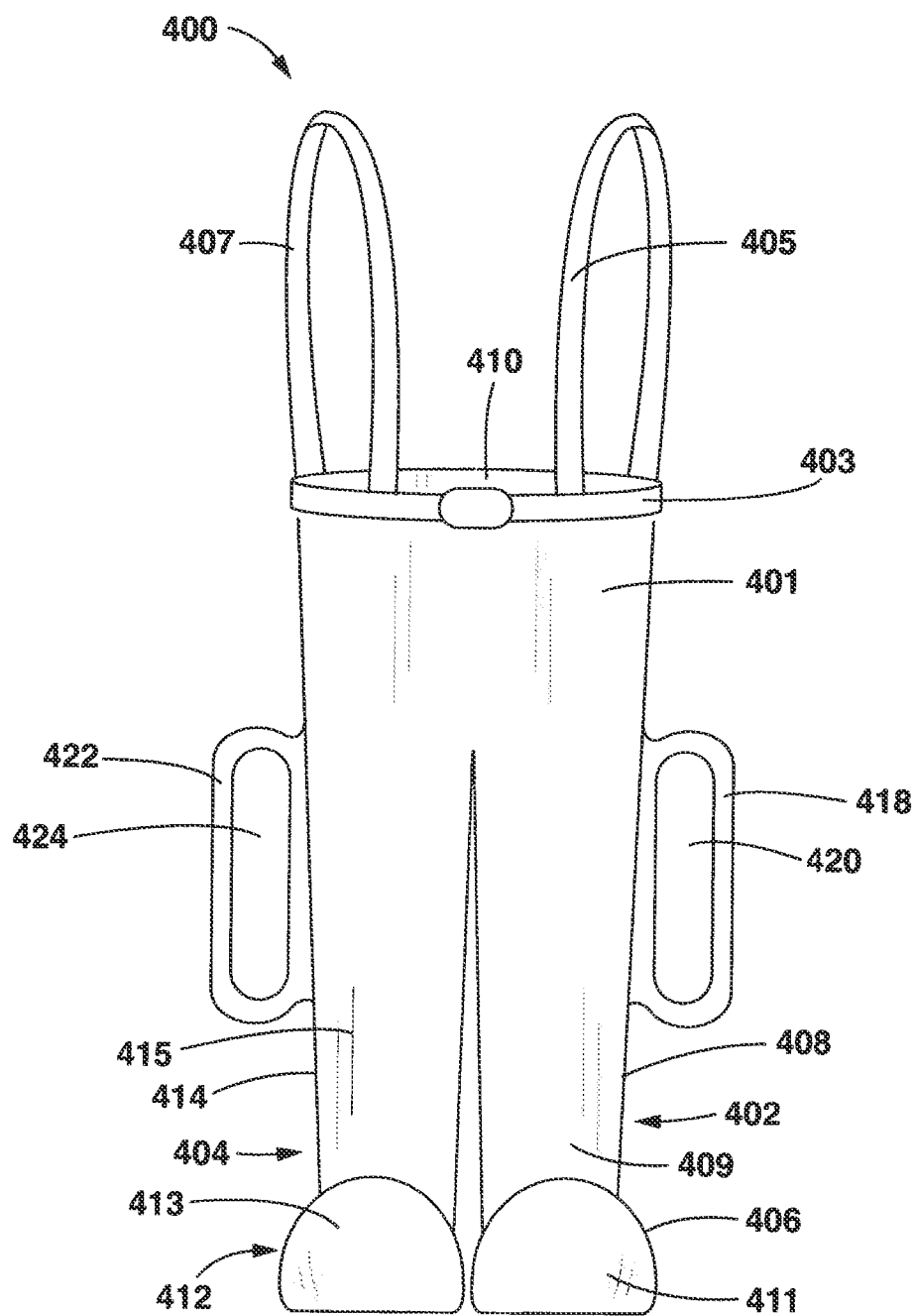
FIG. 4 illustrates an example therapeutic device, in accordance with an embodiment of the present invention.

FIG. 4 illustrates an example therapeutic device, in accordance with an embodiment of the present invention.

A therapeutic device 400 includes a pelvic portion 401, a left portion 402 and a right portion 404.

Therapeutic device 400 receives body portions (not shown) of a person (not shown) for the purpose of cooling the body portions in order to provide therapeutic treatment.

Pelvic portion 401 receives pelvic associated portions of a person's body.

A belt 403 attached to pelvic portion 401 affixes or supports therapeutic device 400 about a persons' body.

A strap 405 and a strap 407 attached to pelvic portion 401 provide support for therapeutic device 400 via a person's shoulders (not shown).

Left portion 402 receives a left limb of a person and right portion 404 receives a right limb of a person.

Left portion 402 includes a base portion 406 and an upper portion 408.

Base portion 406 provides a cavity 411 for receiving the left foot (not shown) of a person receiving therapeutic treatment.

Upper portion 408 provides a cavity 409 for receiving the left leg (not shown) of a person receiving therapeutic treatment.

Entry of limb into left portion 402 is enabled via an opening 410.

Right portion 404 includes a base portion 412 and an upper portion 414.

Base portion 412 provides a cavity 413 for receiving the right foot (not shown) of a person receiving therapeutic treatment.

Upper portion 414 provides a cavity 415 for receiving the right leg (not shown) of a person receiving therapeutic treatment.

Left portion 402 includes a receptacle 418 for receiving a cooling device 420 and right portion 404 includes a receptacle 422 for receiving a cooling device 424.

In operation, cooling device 420 and cooling device 424 provide cooling to liquid (not shown) located within therapeutic device 400. Furthermore, cooled liquid provides cooling to limbs of person inserted into therapeutic device 400 for providing therapeutic treatment.

Figure 5A:
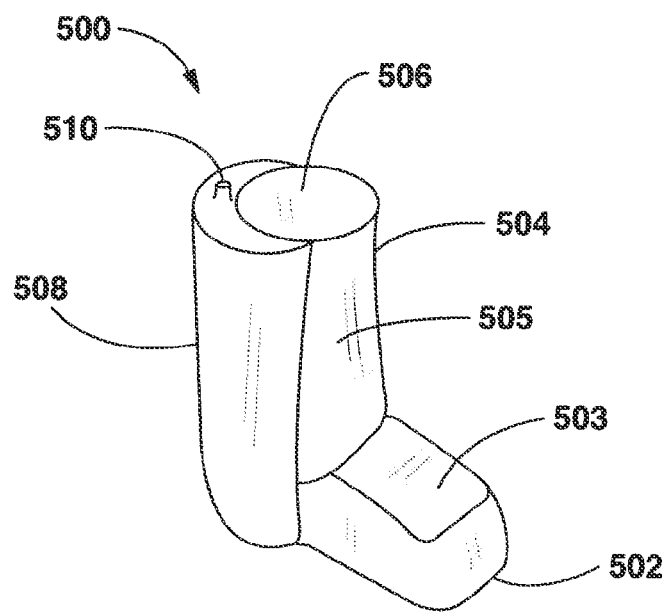
FIGS. 5A-B illustrates an example therapeutic device, in accordance with an embodiment of the present invention.

FIG. 5A illustrates an example therapeutic device, in accordance with an embodiment of the present invention.

A therapeutic device 500 includes a base portion 502 and an upper portion 504.

Therapeutic device 500 receives body portions (not shown) of a person (not shown) for the purpose of cooling the body portions in order to provide therapeutic treatment.

Base portion 502 provides a cavity 503 for receiving a foot (not shown) of a person receiving therapeutic treatment.

Upper portion 504 provides a cavity 505 for receiving a leg (not shown) of a person receiving therapeutic treatment.

Entry of limb therapeutic device 500 is enabled via an opening 506.

A compartment 508 with an opening 510 is attached to upper portion 504.

Compartment 508 provides storage of a liquid.

Opening 510 provides a means for liquid to be placed within compartment 508.

A sealing device provides a means for sealing liquid within compartment 508 by sealing opening 510.

Prior to therapeutic treatment, therapeutic device 500 is placed in a cooler or freezer for cooling or freezing liquid contained in compartment 508.

In operation, cooled or frozen material located in compartment 508 provides cooling to the liquid surrounding the limbs of person inserted into therapeutic device 500 for providing therapeutic treatment.

Figure 5B:
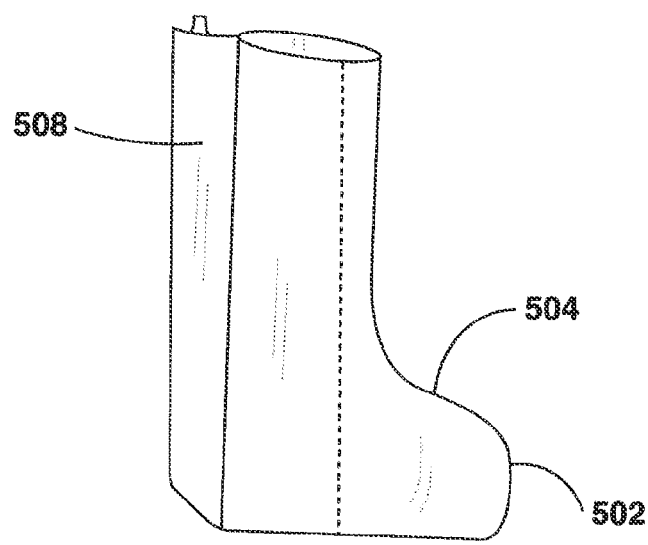

FIG. 5B illustrates a side view perspective of example therapeutic device described with reference to FIG. 5A, in accordance with an embodiment of the present invention.

Figure 6A:
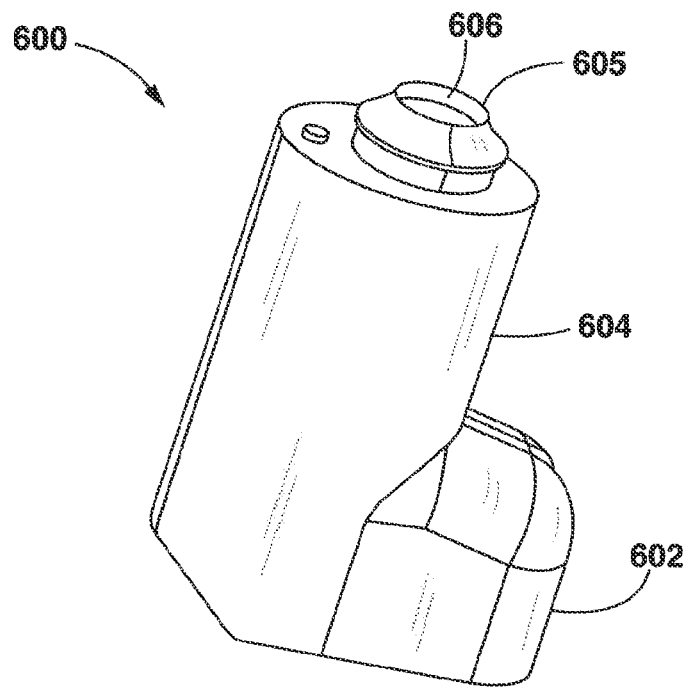
FIGS. 6A-B illustrates an example therapeutic device, in accordance with an embodiment of the present invention.

FIG. 6A illustrates an example therapeutic device, in accordance with an embodiment of the present invention.

A therapeutic device 600 includes a base portion 602, an upper portion 604 and a sealing portion 605.

Therapeutic device 600 receives body portions (not shown) of a person (not shown) for the purpose of cooling the body portions in order to provide therapeutic treatment.

Base portion 602 provides a cavity for receiving a foot (not shown) of a person receiving therapeutic treatment.

Upper portion 604 provides a cavity for receiving a leg (not shown) of a person receiving therapeutic treatment.

Sealing portion 605 provides a means for sealing liquids within therapeutic device 600.

Entry of limb into therapeutic device 600 is enabled via an opening 606.

Figure 6B:
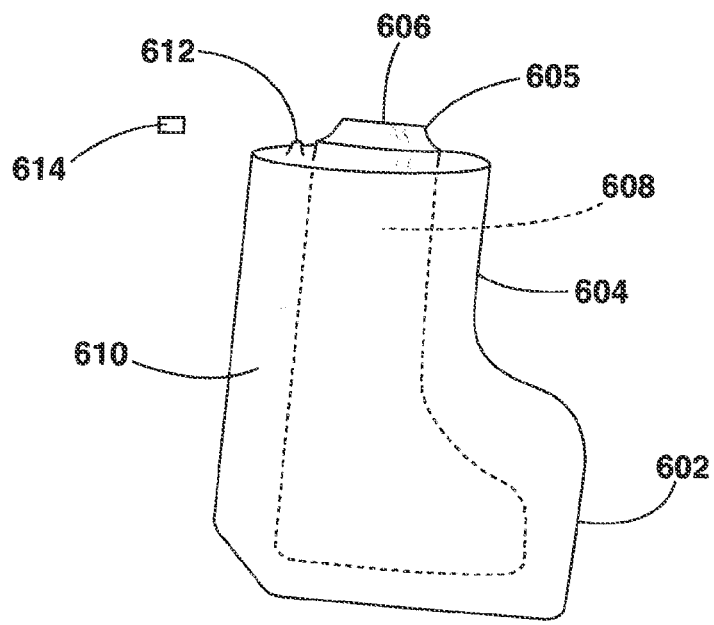

FIG. 6B further illustrates the therapeutic device described with reference to FIG. 6A, in accordance with an embodiment of the present invention.

A cavity 608 and a compartment 610 are located internal to therapeutic device 600.

Cavity 608 provides a cavity for a person's body portion.

Compartment 610 provides a compartment for storage of a liquid. Liquid located within compartment 610 may be converted to a frozen material.

An opening 612 provides a means for entering liquid(s) into compartment 612.

A sealing device 614 provides a means for sealing liquid(s) within compartment 610.

In operation, cooled liquid or frozen material located in compartment 610 provides cooling to the liquid surrounding the limbs of person inserted into therapeutic device 600 for providing therapeutic treatment.

Figure 7A:
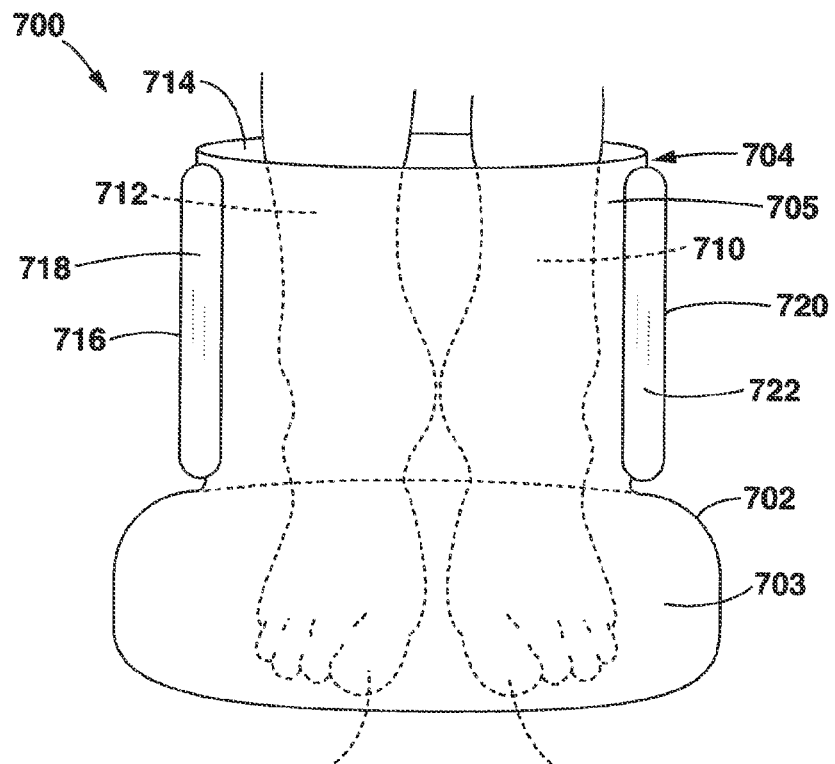
FIGS. 7A-B illustrates an example therapeutic device, in accordance with an embodiment of the present invention.

FIG. 7A illustrates an example therapeutic device, in accordance with an embodiment of the present invention.

A therapeutic device 700 includes a base portion 702 and an upper portion 704.

Therapeutic device 700 receives body portions of a person for the purpose of cooling the body portions in order to provide therapeutic treatment.

Base portion 702 provides a cavity 703 for receiving a left foot 706 and a right foot 708 of a person receiving therapeutic treatment.

Upper portion 704 provides a cavity 705 for receiving a left leg portion 710 and a right leg portion 712 of a person receiving therapeutic treatment.

Entry of body portions into therapeutic device 700 is enabled via an opening 714.

Upper portion 704 includes a receptacle 716 for receiving a cooling device 718 and a receptacle 720 for receiving a cooling device 722.

In operation, cooled liquid or frozen material located within therapeutic device 700 provides cooling to limbs of person inserted into therapeutic device 700 for providing therapeutic treatment.

Figure 7B:
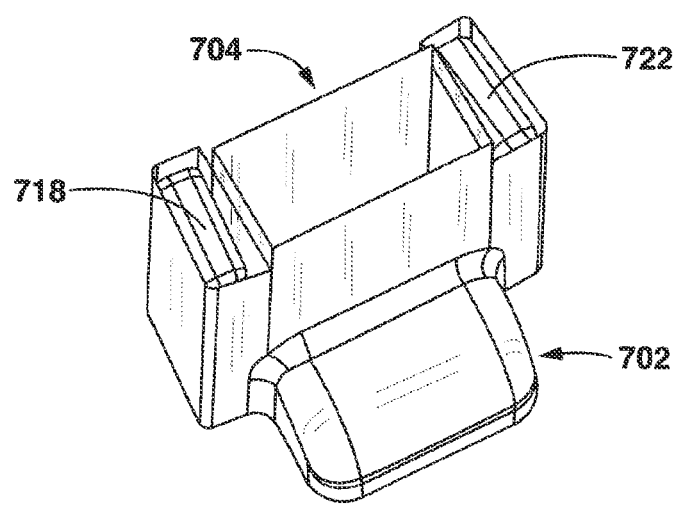

FIG. 7B further illustrates example therapeutic device as described with reference to FIG. 7A, in accordance with an embodiment of the present invention.

Figure 8A:
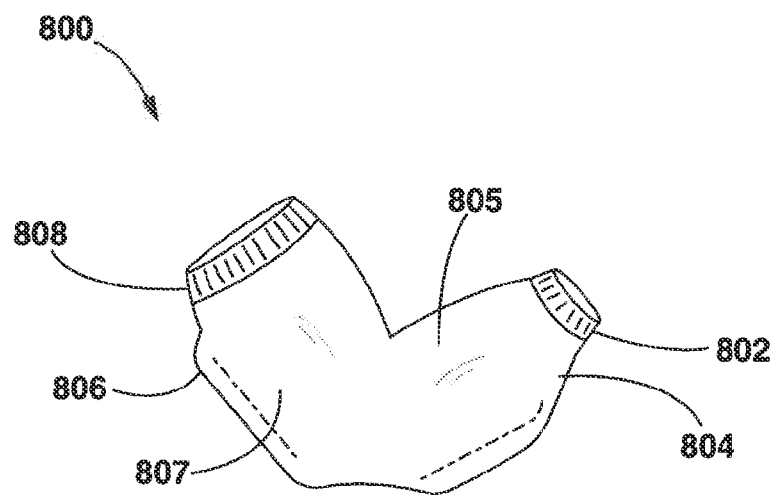
FIGS. 8A-B illustrates an example therapeutic device, in accordance with an embodiment of the present invention.

FIG. 8A illustrates an example therapeutic device, in accordance with an embodiment of the present invention.

A therapeutic device 800 includes a sealing device 802, a lower portion 804, an upper portion 806 and a sealing device 808.

Sealing device 802 and sealing device 808 seal liquid within therapeutic device 800 and/or prevent liquid from being expelled from therapeutic device 800.

Lower portion 804 provides a cavity 805 for receiving a lower arm portion of a person receiving therapeutic treatment.

Upper portion 806 provides a cavity 807 for receiving an upper arm portion of a person receiving therapeutic treatment.

Figure 8B:
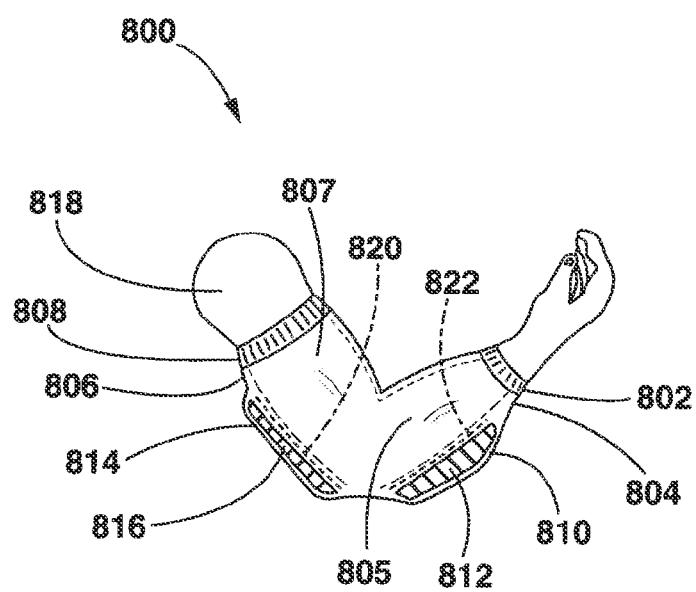

FIG. 8B illustrates more detail of the example therapeutic device described with reference to FIG. 8A, in accordance with an embodiment of the present invention.

Lower portion 804 includes a receptacle 810 for receiving a cooling device 812 and upper portion 806 includes a receptacle 814 for receiving a cooling device 816.

An arm 818 of a person has been inserted into therapeutic device 800.

A divider 820 separates receptacle 814 from cavity 807 and a divider 822 separates receptacle 810 from cavity 805.

In operation, cooling device 812 and cooling device 816 provide cooling to liquid (not shown) located within therapeutic device 800. Furthermore, sealing device 802 and sealing device 808 prevent leakage of liquid contained within therapeutic device 800. Furthermore, cooled liquid provides cooling to limbs of person inserted into therapeutic device 800 for providing therapeutic treatment.

Figure 9A:
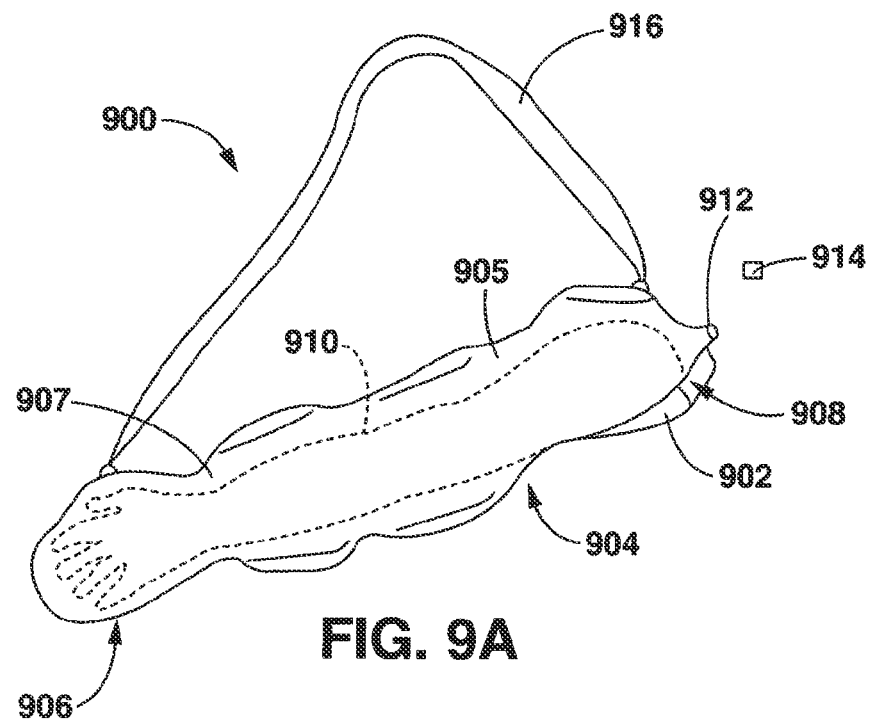
FIG. 9A-B illustrates an example therapeutic device, in accordance with an embodiment of the present invention.

FIG. 9A illustrates an example therapeutic device, in accordance with an embodiment of the present invention.

A therapeutic device 900 includes a sealing device 902, an upper portion 904 and a lower portion 906.

Sealing device 902 seal liquid within therapeutic device 900 and/or prevent liquid from being expelled from therapeutic device 900.

Upper portion 904 provides a cavity 905 for receiving an arm portion of a person receiving therapeutic treatment.

Lower portion 906 provides a cavity 907 for receiving a hand of a person receiving therapeutic treatment.

An opening 908 enables insertion of a limb 910 into therapeutic device 900.

An opening 912 enables insertion of liquid into therapeutic device 900.

A sealing device 914 affixed to opening 912 provides sealing liquid within therapeutic device 900.

A sling/strap device 916 may support some of the weight of the device. A sling/strap device 916 may be placed in a traditional sling manner, around the user's neck/shoulder.

Figure 9B:
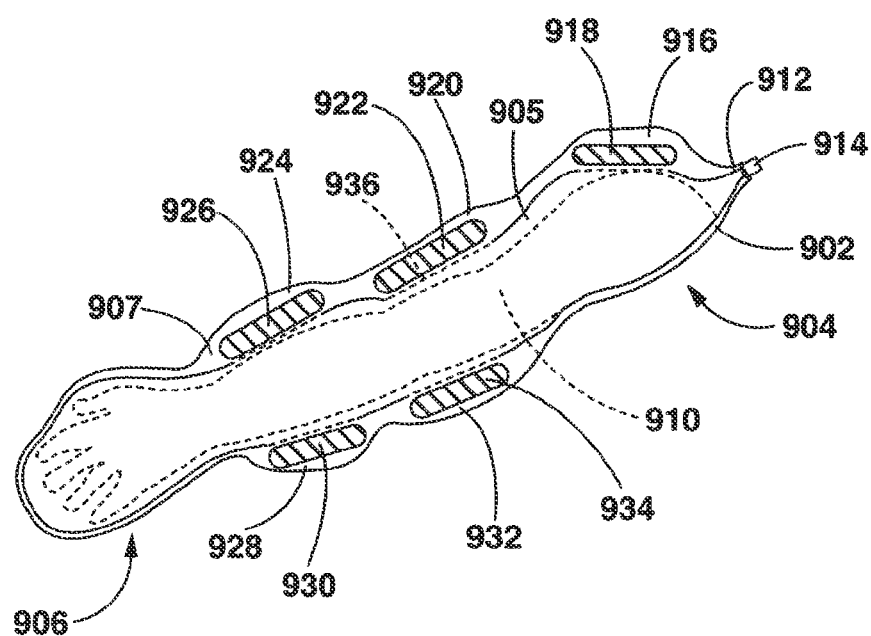

FIG. 9B illustrates more detail of the example therapeutic device described with reference to FIG. 9A, in accordance with an embodiment of the present invention.

Upper portion 904 includes a receptacle 916 for receiving a cooling device 918, a receptacle 920 for receiving a cooling device 922, a receptacle 924 for receiving a cooling device 926, a receptacle 928 for receiving a cooling device 930 and a receptacle 932 for receiving a cooling device 934.

Dividers separate receptacles from cavities. As an example, divider 936 separates receptacle 920 from cavity 905.

In operation, cooling devices 918, 922, 926, 930 and 934 provide cooling to liquid (not shown) located within therapeutic device 900. Furthermore, sealing device 902 prevents leakage of liquid contained within therapeutic device 900. Furthermore, cooled liquid provides cooling to limbs of person inserted into therapeutic device 900 for providing therapeutic treatment.

Figure 10A:
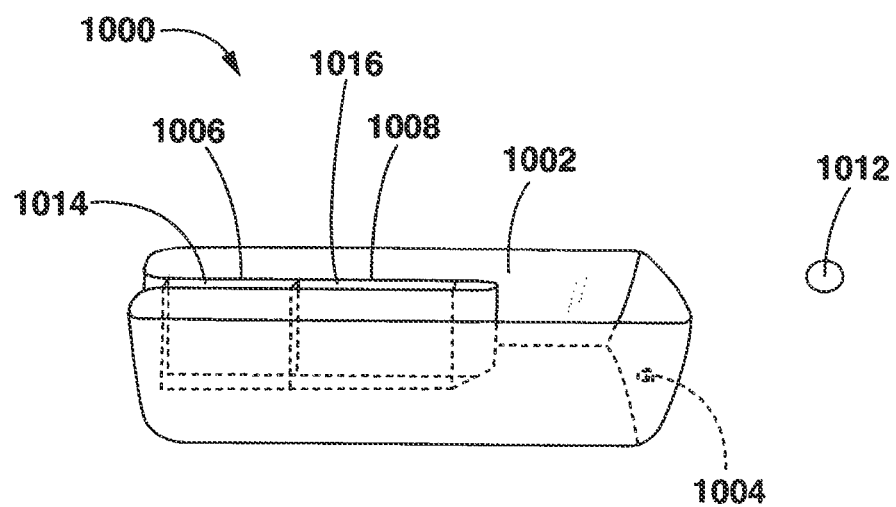
FIGS. 10A-B illustrates an example therapeutic device, in accordance with an embodiment of the present invention.

FIG. 10A illustrates an example therapeutic device, in accordance with an embodiment of the present invention.

A therapeutic device 1000 includes a cavity 1002, a drain 1004, a receptacle 1006 and a receptacle 1008.

Cavity 1002 enables a person to sit or lie in therapeutic device 1000.

Drain 1004 enables exit of liquid retained by therapeutic device 1000. A plug device 1012 prevents exit of liquid (not shown) when inserted into drain 1004 and enables exit of fluid when removed from drain 1004.

Receptacle 1006 enables insertion of a cooling device 1014.

Receptacle 1008 enables insertion of a cooling device 1016.

In operation, cooling device 1014 and cooling device 1016 provide cooling to liquid (not shown) located within therapeutic device 1000. Furthermore, cooled liquid provides cooling to the body of a person sitting or lying in therapeutic device 1000 for providing therapeutic treatment.

Figure 10B:
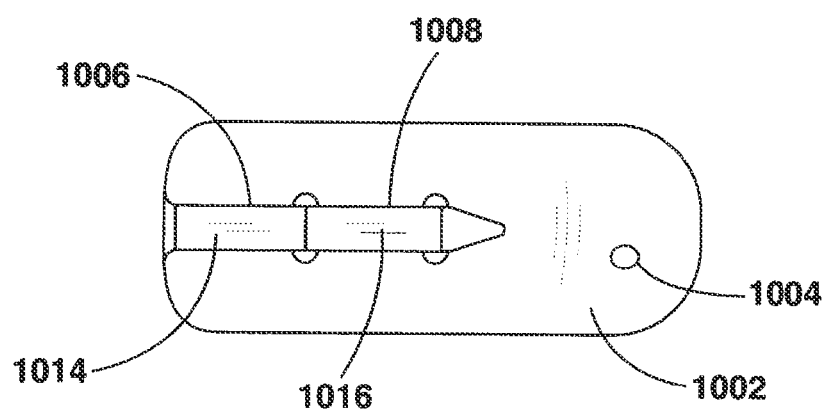

FIG. 10B illustrates a top view of the example therapeutic device described with reference to FIG. 10A, in accordance with an embodiment of the present invention.

FIGS. 11A-C illustrates an example therapeutic device, in accordance with an embodiment of the present invention. FIG. 11A illustrates a side view. FIG. 11B illustrates a front view. FIG. 11C illustrates a top view.

A therapeutic device 1100 includes a cavity 1102, a receptacle 1106 and a receptacle 1108.

Contour 1104 and cavity 1102 enables a person to place their neck and head in therapeutic device 1000 while in a supine position. Contour 1104 provides a seal about a portion of the person's neck to prevent liquid (not shown) from exiting cavity 1102 when the person's head displaces a volume of the liquid.

Receptacle 1106 enables insertion of a cooling device 1114.

Receptacle 1108 enables insertion of a cooling device 1116.

Pad 1120 may be included for additional comfort of the person. In some embodiments ear plugs may be used by the person.

In operation, cooling device 1114 and cooling device 1116 provide cooling to liquid (not shown) located within therapeutic device 1100. Furthermore, cooled liquid provides cooling to the neck and head of a person lying in therapeutic device 1100 for providing therapeutic treatment. In a non-limiting example, the therapeutic treatment may be for migraine headaches.

Figures 12A, 12B:
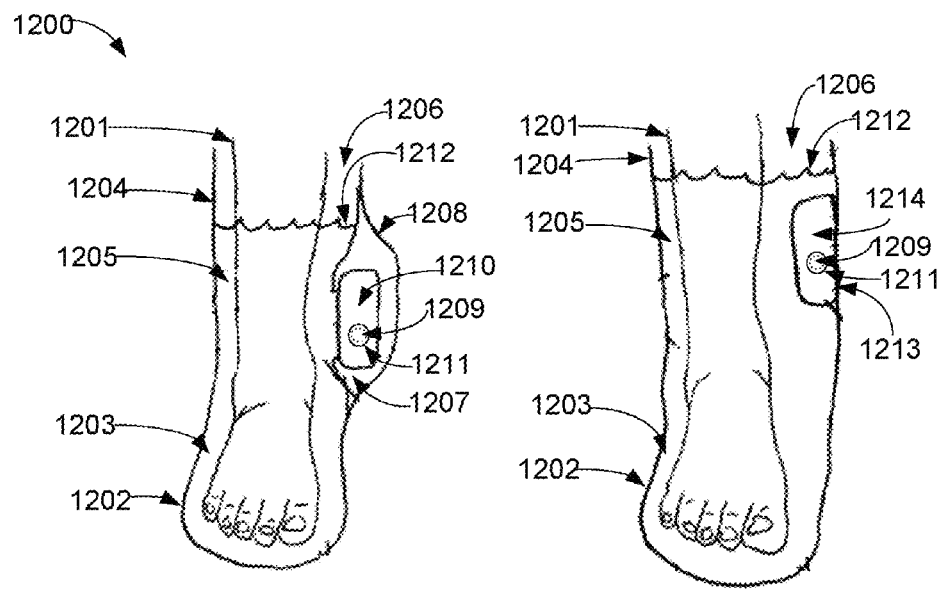
FIGS. 12A-D illustrates an example therapeutic devices, in accordance with an embodiment of the present invention.

FIG. 12A illustrates an example therapeutic device, in accordance with an embodiment of the present invention.

A therapeutic device 1200 includes a base portion 1202 and an upper portion 1204.

Therapeutic device 1200 receives a body portion 1201 of a person for the purpose of cooling the body portions in order to provide therapeutic treatment.

Base portion 1202 provides a cavity 1203 for receiving a foot of body portion 1201 for the person receiving therapeutic treatment.

Upper portion 1204 provides a cavity 1205 for receiving a leg of body portion 1201 for the person receiving therapeutic treatment.

Entry of body portion 1201 into therapeutic device 1200 is enabled via an opening 1206.

A pocket 1207 of a receptacle 1208 receives a cooling device 1210.

A liquid 1212 may be instilled within cavity 1203 and cavity 1205 via opening 1206.

Cooling device 1210 may be instilled with liquid (not shown) via an opening 1209 when a sealing device 1211 is not attached to opening 1209. Furthermore, cooling device 1210 may be sealed from leakage of liquid from cooling device 1210 via application of sealing device 1211 to opening 1209.

Prior to therapeutic treatment, cooling device 1210 is placed in a cooler or freezer for cooling or freezing liquid contained in cooling device 1210.

In operation, cooled or frozen material located in cooling device 1210 provides cooling to limbs of person inserted into therapeutic device 1200 for providing therapeutic treatment. Furthermore, liquid 1212 is in direct contact with portions of cooling device 1210 enabling exchange of heat between liquid 1212 and cooling device 1210.

FIG. 12B illustrates an example therapeutic device, in accordance with an embodiment of the present invention.

A receptacle 1213 receives a cooling device 1214.

The surface area of cooling device 1214 contacting liquid 1212 is greater for FIG. 12B than as compared to FIG. 12A.

Figures 12C, 12D:
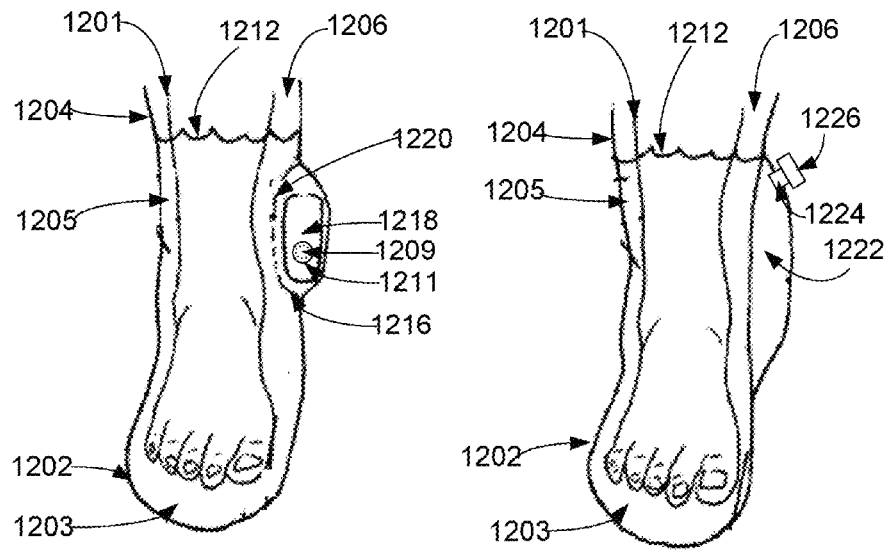

FIG. 12C illustrates an example therapeutic device, in accordance with an embodiment of the present invention.

An enclosed receptacle 1216 receives a cooling device 1218.

Cooling device 1218 makes contact with liquid 1212 via interchange of liquid 1212 through a membrane 1220. As a non-limiting example, membrane 1220 may be configured of a mesh material.

FIG. 12D illustrates an example therapeutic device, in accordance with an embodiment of the present invention.

A cooling chamber 1222 provides heat exchange with liquid 1212.

Cooling chamber 1222 may be instilled with liquid (not shown) via an opening 1224 when a sealing device 1226 is not attached to opening 1224. Furthermore, cooling chamber 1222 may be sealed from leakage of liquid from cooling chamber 1222 via application of sealing device 1226 to opening 1224.

The present invention provides means by which a person's body or portions of a person's body may be cooled. As a non-limiting example, feet/ankles/legs, the entire lower extremity or the entire lower body. Furthermore, the waist, upper extremities or portions of upper extremities can be cooled rapidly and symmetrically. As a non-limiting example, cooling of body or body portions may be as a result of injury or athletic activity. Furthermore, cooling may be performed via submersion of the extremity or extremities or body parts into an extremity cavity or cavities. Cavities 107 (FIG. 1), 109 (FIG. 1), 113 (FIG. 1), 115 (FIG. 1), 307 (FIG. 3), 309 (FIG. 3), 313 (FIG. 3), 315 (FIG. 3), 407 (FIG. 4), 409 (FIG. 4), 413 (FIG. 4), 415 (FIG. 4), 503 (FIG. 5), 505 (FIG. 5), 608, 703 (FIG. 7), 705 (FIG. 7), 805 (FIG. 8), 807 (FIG. 8), 905 (FIG. 9), 907 (FIG. 9), 1002 (FIG. 10), 1102 (FIG. 11), and 1203 (FIG. 12) provide space for cooled liquid to surround areas of the inserted body parts for providing therapeutic treatment. As a non-limiting example, therapeutic treatment may be provided symmetrically. As a non-limiting example, the extremity receptacles may be fabricated of liquid impermeable material. Non-limiting examples of liquid impermeable material include plastic or other rigid/semi-rigid material such as rubber or neoprene. Furthermore, any known liquid-impermeable material may be used for receptacles. Typically, receptacles do not provide direct contact with the extremity or extremities. In some cases, a receptacle may come in direct contact with an extremity or extremities such as where a foot or the feet may rest on the base of the receptacle. Furthermore, the option of direct contact between a body portion and a receptacle may be chosen by a user. The receptacle may roughly mirror the shape of an inserted extremity, but with sufficient space between the cavity and inserted body part for liquid to surround the inserted extremity or body part. A cavity can be used for one limb as described with reference to FIGS. 5, 6, 8, 9 and 12. A cavity can be used for a neck and head as described with reference to FIG. 11. Furthermore, a cavity may accommodate multiple extremities as described with reference to FIG. 7. Furthermore, a therapeutic device may provide separate cavities for a multiplicity of limbs as described with reference to FIGS. 1, 2, 3, 4 and 10.

In other embodiments, separate single extremity embodiments may be attached for providing therapeutic treatment for multiple limbs.

The liquid placed within the cavities may be cooled by cooling devices 120 (FIG. 1), 124 (FIG. 1), 228 (FIG. 2), 232 (FIG. 2), 320 (FIG. 3), 324 (FIG. 3), 420 (FIG. 4), 424 (FIG. 4), 718 (FIG. 7), 722 (FIG. 7), 812 (FIG. 8), 816 (FIG. 8), 918 (FIG. 9), 922 (FIG. 9), 926 (FIG. 9), 930 (FIG. 9), 934 (FIG. 9), 1014 (FIG. 10), 1016 (FIG. 10), 1114 (FIG. 11), and 1116 (FIG. 11). Non-limiting examples for means for providing cooling includes ice, ice blocks, gel or chemical inserts. Furthermore, cavities may be cooled via frozen material (or other cooling material) in separate self-contained, liquid-tight compartments 508 (FIG. 5) 610 (FIG. 6), 1210 (FIG. 12), 1214 (FIG. 12), 1218 (FIG. 12) and 1222 (FIG. 12) located with the therapeutic device housing. Furthermore, the cooling devices or compartments containing frozen material/cooling liquid contact the liquid surrounding the body portion or body portions. Furthermore, a divider may surround body portion or portions. Non-limiting examples for a divider include a space, mesh, or liquid permeable divider (e.g. dividers 126 (FIG. 1), 128 (FIG. 1), 234 (FIG. 2C), 236 (FIG. 2C), 820 (FIG. 8), 822 (FIG. 8) and 936 (FIG. 9). Furthermore, divider may provide a conduit for transfer of heat.

In one embodiment, the cooling device is chilled by placing at least the cooling device into a refrigeration device. In another embodiment, the cooling device is chilled by placing the cooling device and the therapeutic cooling apparatus into the refrigeration device.

Cooling devices, ice blocks or cold compartments can be of any known shape or size. Non-limiting examples for material used for cooling devices include inserts plastic, rubber or other liquid-resistant material. The cooling devices may contain liquid for freezing or cooling, or other material capable of being frozen or cooled (e.g. cooling gel or a solid). As a non-limiting example, liquid may be water. Cooling devices may also contain materials capable of an endothermic reaction. Cooling devices and compartments may contain a seal or twist top for sealing an opening used for instilling liquid or other material into the devices or compartments.

Therapeutic device housing can be configured to receive frozen liquid bottles or even larger frozen containers (e.g. frozen milk jugs or large ice blocks) for larger device embodiments, such as described with reference to FIG. 4 and FIG. 10. A multiplicity of cooling devices, ice blocks and/or cold compartments may be configured for inserting into therapeutic device. Furthermore, cooling devices, ice blocks and/or cold compartments can be configured for a multiplicity of locations as described with reference to FIGS. 1-12. Furthermore, cooling devices, ice blocks can be located on the exterior of a cavity. Cooling devices or cold compartments may encompass the cavity as described with reference to FIG. 6. Cooling devices or cold compartments can be located between cavities as described with reference to FIGS. 1-3. In some alternate embodiments, the therapeutic housing itself may be the cooling device. In these embodiments the housing comprises one or more portions that may be frozen or cooled.

In some embodiments, the therapeutic device is maintained relatively stationary and not designed for ambulation. In other embodiments, the therapeutic device may allow limited ambulation by being fabricated of flexible materials. Non-limiting examples of flexible materials include rubber, neoprene and liquid resistant fabric.

For a rigid or semi-rigid therapeutic device housing or for rigid or semi-rigid portions of therapeutic device housing, the rigid nature of the device maintains the device in an upright position. Furthermore, the rigid or semi-rigid device housing provides for a flat or reclining position for a supine/sitting embodiment, as described with reference to FIG. 10 and FIG. 11.

Furthermore, the therapeutic device housing provides structure and maintains the cooling devices or chambers in place and with a sufficient distance from the inserted extremity so as to provide room for instilled liquid and subsequent heat exchange between the inserted body part and the cooled liquid.

Cooling devices may be maintained within receptacles via a lip or ridge. Furthermore, other structures may be provided for holding cooling devices in place. Non-limiting examples for other structures includes a wall or mesh.

Furthermore, cooling devices may be held in place by the general shape of the extremity receptacle itself and/or by the shape of the device housing. Furthermore, the cooling devices may be held in place by latching mechanisms between the device housing and the cooling devices. Non-limiting examples for latching mechanism include interlocking or any other known method for attaching devices together.

Therapeutic device housing that may be configured in the shape of the inserted body portion or may deviate from the shape of the inserted body portion.

Therapeutic device housing may or may not follow the general shape of the cavity. Furthermore, the therapeutic device housing may form the structure for the cavity or may form a portion of the cavity structure.

Therapeutic device housing base may also be extended in order to provide for additional stability for keeping the device upright.

Furthermore, therapeutic device housing may be extended upward in order to provide additional depth for submerging additional body portions.

The base of therapeutic device housing may be configurable for facilitating comfort for the person being treated. As a non-limiting example, a flat portion of the heel angled upward from the horizontal base provides stability of the apparatus while the person being treated may be sitting on the ground. Furthermore, angling of the heel provides increased comfort for user.

Furthermore, a sealable flap or tight fitting ring encircling the extremity at the point where the extremity protrudes from the therapeutic device may be provided in order to prevent spillage of liquid from the device.

Therapeutic device may be configured such that cooling device or compartment does not contact body portions. Furthermore, the heat is passively transferred through liquid encapsulating the submerged body portion to the cooling device or cooling chamber. Furthermore, the cooling process may be performed in a symmetrical fashion. Furthermore, a multiplicity of body portions may be cooled simultaneously and in a convenient manner.

Therapeutic device provides uniform cooling of body or body portions as a result of liquid heat conduction.

Furthermore, therapeutic device provides ease of use via convenient, reusable cooling devices or cooling chambers.

Therapeutic device provides body portions with submersion and contact with liquid.

Therapeutic device provides space between body portions and device structures in order to decrease potential for additional injury and to provide for patient comfort.

Therapeutic device allows for large areas of a single extremity or a multiplicity of extremities to be treated simultaneously.

Therapeutic device enables cold therapy in a multiplicity of venues. Non-limiting examples of venues include outdoor or at athletic events.

As a non-limiting example, therapeutic device may be used for athletes and by trainers for persons with a lower extremity injury. As a non-limiting example, therapeutic may be used for injuries and ailments associated with sports such as football, basketball, running, triathlon, biking and endurance associated sports. As a non-limiting example, device may be used for institutional settings such as hospitals, training facilities, sports medicine clinics, orthopedics clinics and ERs. Furthermore, as a non-limiting example, organizers of athletic racing events may use therapeutic device following an event. Non-limiting examples of ailments for which the therapeutic device may be deployed include plantar fasciitis, Achilles tendonitis, shin splints, ankle sprains, muscle strains and other lower extremity injuries.

As a non-limiting example, therapeutic device may be used for applying cold therapy for upper extremity. Non-limiting examples of upper extremity ailments therapeutic device may be used for include pitcher's elbow, tendonitis, arthritis, tenosynovitis, shoulder injuries and bursitis.

As described with reference to FIGS. 3-4, 9, larger, more extended embodiments of the therapeutic device with extension over the waist may be used for weight loss applications. As a non-limiting example, larger embodiments of the therapeutic device may be placed in the shower and used on a daily basis for therapy directed toward weight loss or previously discussed athletic associated applications. Non-limiting examples for use of therapeutic device associated with heat injuries include heat exhaustion, hyperthermia and heat.

Therapeutic device provides a light-weight, effective for application of cold therapy methods.

Therapeutic device provides enough space in cavities in order for limbs to be comfortable inserted into the device and not physically touch the device.

Therapeutic device provides enough space for liquid such that adequate heat exchange occurs with the inserted extremity, but not too much space such that the device is heavy or inconvenient for use.

Therapeutic device is configured in order to provide stability such that a user may be use the device in a multiplicity of different positions.

In some embodiments, therapeutic device may be configured for application by a user sitting on a chair above the device. Furthermore, the device may be configured with flat surfaces on the external structure in order to provide user comfort and stability.

Cooling devices may be configured for any known shape, size or consistency. Furthermore, cooling devices provide cooling for several hours after removal from a freezer or cooler.

The configuration of the cooling devices aid in ease of transportation to events (e.g. sporting events).

Therapeutic device and associated cooling devices are fabricated of materials resistant to damage from repeated temperature change. Furthermore, the therapeutic device and associated cooling devices are configured to compensate for expansion and contraction of the materials with temperature change.

Therapeutic device may be used in a multiplicity of settings. As an example, an athlete may use the device following a workout for preventive cold therapy or for injury therapy.

Furthermore, as described with reference to FIGS. 5, 6, 8, 9 a user may place an extremity into the cavity of the therapeutic device. Furthermore, as described with reference to FIGS. 1, 2, 3, 4, 7, 10, and 11 a user may place a multiplicity of limbs or body parts into the cavities of the therapeutic device. Furthermore, a user may access therapeutic device from a multiplicity of configurations, sitting on a chair, sitting on ground, lying on ground and standing.

Embodiments of therapeutic device configured with rigid device housing such as plastic may be configured for stationary application while in use, but light enough for ease of movement or transportation while not in use.

Therapeutic device may be used outdoors following athletic events. Furthermore, therapeutic device may be used indoors or in vehicles of transportation.

In operation, users may insert cooling devices into the receptacles associated with the therapeutic device. Furthermore, liquid may be poured or instilled into device. Furthermore, body portions may be inserted into therapeutic device. Furthermore, inserted cooling devices are configured such that the devices do not physically touch inserted body portions. Instilled or inserted liquid provides cooling to the extremities via transfer of heat from the extremities, into the liquid and into the cooling devices.

Cooling devices are configured such that significant heat transfer is performed secondary to the direct contact with the liquid surrounding the extremity. Furthermore, the interior structure of the device provides sufficient space such that the inserted body portion does not physically contact with the sides, housing or cooling devices.

Cooling devices not making direct contact with the inserted extremity enables symmetric and diffuse cooling via the liquid interface between the cold/frozen cooling device and the inserted extremity located in the cavity. Furthermore, the extremity may be cooled evenly via the configuration of the device and the associated the cold liquid.

Movement of the users' extremities within the therapeutic device may operate to circulate the cold liquid providing further equalization of temperatures throughout the liquid and speeding heat transfer.

Following application of cold therapy via the therapeutic device for the prescribed time, the extremities can be removed from the device. As a non-limiting example, the timeframe for performing therapy may be 10 minutes. Furthermore, after use, therapeutic may be reused by another user. Furthermore, the cooling devices may be refrozen for later use.

For embodiments of the present invention with chamber configurations as described with reference to FIGS. 5-6 and 12, the user may fill the chamber to a predetermined level, seal that chamber (e.g. via twist top or other mechanism) and place the entire device in the freezer.

The chamber is configured for leak resistance and allows for expansion as the instilled liquid freezes.

In other embodiments, chamber may be partially filled in order to compensate for expansion associated with the frozen material.

Following exercise or injury, chamber configured therapeutic device would be removed with the previously placed material/liquid in the chamber now frozen or cooled. Furthermore, user would place liquid into the cavity. Furthermore, the limb, limbs or body portions(s) are then placed into the cavity with subsequent performance of cooling therapy.

For the therapeutic device discussed with reference to FIG. 5A-B, the compartment encircles the cavity in order to maximize contact/surface interface between the cooling compartment and the cavity.

For the therapeutic device discussed with reference to FIG. 6, the chamber encompasses the cavity.

Non-limiting examples for configuration of chambers include multiple ice/frozen chambers with a multiplicity of locations for supporting a variety of configurations for cavities.

In other embodiments, cooling devices may be interchangeable with chambers and vice-versa.

As described with reference to FIGS. 3-4, a user may stand in a therapeutic device such that the device extends above the knee, hip or waist of the user. Furthermore, the cooling devices illustrated in FIGS. 3-4 are configured large enough to accommodate the extended size of the therapeutic devices and the increased amount of associated liquid for providing heat exchange.

Furthermore, the extended height therapeutic device may be configured with a wider based in order to provide stability. Furthermore, user may be provided with a support for holding to compensate for the extended height. The extended height therapeutic device simultaneously enables the lower body portion to be subjected to therapy.

Furthermore, the extended height therapeutic device may be configured with wheels for ease of movement. Furthermore, the wheels may be associated with the base or the device housing. Furthermore, adherent devices located on the underside of the base aid in preventing slippage of the device. As a non-limiting example, slippage may be prevented while therapeutic device is located in a shower.

Extended height therapeutic device may be used for weight loss applications as large portions of body portions may be cooled.

As a non-limiting example, extended height therapeutic device may be filled with liquid in a shower and used in a shower. For shower use, large cooling devices or blocks of ice may be placed in the device. Furthermore, the device may be filled with water from the shower. Furthermore, a user may insert body portions in to cavity for performance of therapy. Furthermore, liquid may be expelled or drained from therapeutic device by removing sealant device from drain. Furthermore, liquid contained within therapeutic device may be expelled without tipping device.

Therapeutic devices may be configured with flexible housing material as illustrated with respect to FIGS. 3, 4, 8, 9. Furthermore, flexible housing material enables movement of body portions located within therapeutic device. Non-limiting examples for flexible housing material include neoprene, rubber, or liquid resistant.

Additional structural material may be configured for therapeutic devices with flexible housing material in order to allow for sufficient space for liquid between the extremity inserted in the cavity and the cooling devices. Furthermore, this configuration provides separation between cooling devices and body portions.

As described with reference to FIG. 4, suspenders or other over the shoulder straps may be configured such that the device remains in place while a user walks or moves about. Furthermore, a belt or strap about the waist area may be used for additional support. Furthermore, space is provided between the cooling devices. Furthermore, the location of the cooling devices provides for more ease of movement. Furthermore, cooling devices may be configured in a multiplicity of locations and may be of a multiplicity of sizes, shapes or material. Furthermore, in some cases, a base may not be configured for therapeutic device.

As discussed with reference to FIGS. 8A-B, therapeutic device may be used for the upper extremity. Non-limiting examples for upper extremity include hand, wrist, elbow or areas adjacent to the elbow. Furthermore, therapeutic device housing and associated cavity can be configured with a multiplicity of seals. Furthermore, therapeutic device may be applied mid-extremity with limited spillage of liquid from the device.

Furthermore, therapeutic device may be applied to the knee or other mid-extremity locations.

Furthermore, therapeutic device may be configured with flexible material to enable movement of the body portion(s). A multiplicity of cooling devices may be configured with an associated multiplicity of locations. Cooling devices may be held in place via a mesh material. Cooling devices may be inserted into cavities via externally located openings. Furthermore, external openings may be sealed via a sealing mechanism. As a non-limiting example, sealing mechanism may be configured as a zipper device.

As discussed with reference to FIG. 9, a therapeutic device encompasses an upper extremity. Furthermore, the device housing may be configured of flexible material. Furthermore, a multiplicity of cooling devices with associated receptacles may be configured in a multiplicity of locations. Furthermore, sufficient space is provided to allow for liquid to conduct between the body portion and the cooling devices. Furthermore, liquid is instilled after the device is secured about the extremity via a flap or seal. Furthermore, liquid may be instilled in the device prior to insertion of the body portion and then topped off. Furthermore, opening for instilling liquid may be sealed using a sealing device. Furthermore, instilling of liquid via opening ensures body portion is encapsulated by the liquid.

The device as shown in FIG. 9 and its attachments may also extend to encompass some portion of the chest to allow for better attachment to and treatment of the shoulder and proximal upper extremity. These attachments or seals could also extend all the way around and encompass the chest wall or portions of the neck.

As discussed with reference to FIGS. 10 and 11, a therapeutic device may be provided with an opening at the top such that a user may sit or recline within device. Furthermore, the device may be configured in order to conform to the contours of a bathtub. Furthermore, the device may be configured for location on a flat surface. Furthermore, a multiplicity of cooling devices may be inserted into an associated multiplicity of receptacles with a multiplicity of locations.

Furthermore, in operation, therapeutic device may be located in a bathtub. Furthermore, cooling devices may be inserted into receptacles. Furthermore, liquid may be inserted into cavity of device. Furthermore, body portions may be inserted into cavity for providing therapeutic treatment. Furthermore, liquid may be expelled via a drain. Furthermore, therapeutic device may be placed in the bathtub with cooling devices inserted into receptacles. Furthermore, therapeutic may be filled with liquid for performing exchange of heat. Furthermore, user may sit in device for receiving therapy. Furthermore, liquid associated with therapeutic device may expelled into a bathtub. Furthermore, adherence devices may be attached to bottom of device to aid in preventing slippage of the device in a bathtub. Furthermore, therapeutic device may be used on a flat surface.

In some embodiments, therapeutic device provides a cavity or cavities for receiving body portions for providing therapeutic treatment. Therapeutic device provides a receptacle or receptacles for receiving a cooling device or cooling devices. Cooling device or cooling devices provide for heat exchange with liquid in contact with body portion or body portions.

In other embodiments, a chamber or chambers is/are configured for receiving a liquid. Furthermore, therapeutic device may be placed in freezer for converting liquid to a frozen matter. Chamber or chambers provide for heat exchange with liquid in contact with body portion or body portions.

In some embodiments, a mesh structure may be integrated into the rigid housing of a therapeutic device in order to provide a receptacle or receptacles for cooling device(s). Furthermore, a multiplicity of mesh receptacles may be configured for a multiplicity of locations. Non-limiting examples for cooling devices include ice, ice blocks and cold inserts.

In other embodiments, a therapeutic device may be configured for accommodating a multiplicity of persons simultaneously.

In other embodiments, insulation may be configured with therapeutic device housing.

In other embodiments, a collapsible or partially collapsible therapeutic device may be configured. Collapsible or partially collapsible device enables ease of storage and transport when not in use.

In other embodiments, therapeutic device may be inflatable.

Structure for the therapeutic device housing may be configured with rigid bars/rods. Furthermore, bars/rods may be collapsible or telescopic. Furthermore, bars/rods provide a structure for a liquid impermeable fabric, plastic or membrane. Furthermore, fabric, plastic or membrane may be used to provide receptacles for receiving cooling devices.

Housing for therapeutic device may be expanded to support a multiplicity of cavities for a multi-user application.

Housing structure for therapeutic device may extend beyond the hips or waist of a person and may include suspenders or built-in straps for retaining the impermeable fabric or membrane.

Therapeutic device may be configured with wheels and extendable handles for ease-of-transport (e.g. extendable handles similar to extendable handles used for luggage)

Furthermore, larger therapeutic devices may have gripping devices configured on the bottom side of the device. Furthermore, gripping devices aid in providing stability in the shower or other surfaces. As a non-limiting example, gripping devices may be configured of rubber.

An inserted body portion may be inserted into an impermeable bag prior to placement in its associated cavity in order to maintain the dryness of the body portion. As a non-limiting example, impermeable bag may be configured of a plastic material.

Figure 13:
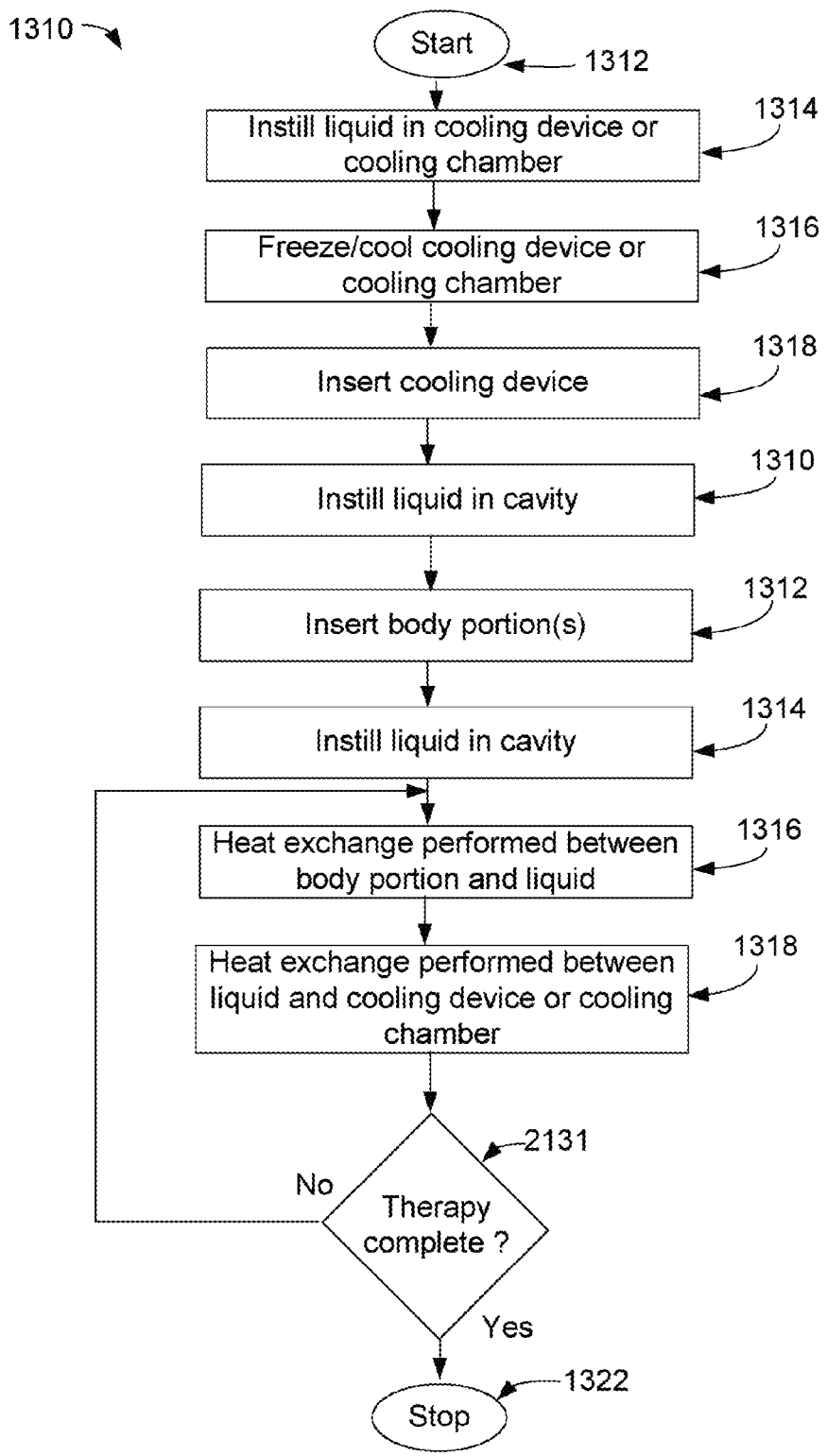
FIG. 13 illustrates an example for a method for operation of a therapeutic device, in accordance with an embodiment of the present invention.

FIG. 13 illustrates an example for a method for operation of a therapeutic device, in accordance with an embodiment of the present invention.

FIG. 13 presents a flow chart for a method 1300 initiating in a step 1302.

In step 1302, liquid may be instilled in cooling devices or cooling chambers of the therapeutic devices that comprise cooling devices or chambers that require filling.

In a step 1304, liquid may be instilled into a cooling device of a therapeutic device that comprises an opening with a sealing device. After instilling liquid into the cooling device, the sealing device may be attached to the opening to prevent leaking of liquid.

In a step 1306, the cooling device(s), cooling chamber, and/or therapeutic device may be placed in cooler or freezer for cooling or freezing liquid or material instilled within the respective devices.

In a step 1308, cooling device or cooling chamber may be removed from cooler or freezer and inserted into receptacle. Furthermore, therapeutic devices with associated cooling chambers may be removed from cooler or freezer. Additionally, therapeutic devices or housings that are constructed of one or more cooling device portions may be removed from the cooler or freezer.

In a step 1310, liquid may be partially instilled in the cavity or cavities of the therapeutic device.

Liquid may be partially instilled in order to provide lubrication for insertion of body portion(s). Furthermore, enough liquid may be instilled such that spillage is avoided when body portion(s) is/are inserted into the therapeutic device. In some embodiments, partially instilling the liquid may not be done.

In a step 1312, body portion(s) is/are inserted into the cavity or cavities of the therapeutic device. In some embodiments, a water impermeable membrane or plastic may be placed about the body part prior to insertion into the therapeutic device.

In a step 1314, liquid may be instilled into the cavity or cavities of the therapeutic device to surround the body portion(s).

In a step 1316, heat exchange is performed between body portion(s) and liquid in the cavity or cavities surrounding the body portion(s).

The liquid is at a lower temperature than the body portion and operates to remove heat from the body portion thereby producing a therapeutic effect for body portion.

In a step 1318, heat is exchanged between the liquid surrounding the body portion(s) and the cooling device(s) or cooling chamber(s.

The temperature of the cooling device or cooling chamber is lower than the temperature of the liquid and operates to remove heat from the liquid.

In a step 1320, a determination may be performed for completion of therapy. For not completing therapy, method 1300 transitions to step 1316 and for completion of therapy, method 1300 transitions to a step 1322 resulting in termination for the execution of method 1300.

Method 1300 may be used in a wide array of settings. As a non-limiting example, athletes following a workout for preventive cold therapy. As another non-limiting example, athletes with an injury for injury therapy. User may place an extremity or any body part into the therapeutic device for cooling the body portion or portions. Liquid in the cavity or cavities performs cooling of the body portion or portions via transfer of heat from the body portion to the liquid. Furthermore, heat is transferred from liquid to cooling device or cooling compartment. Furthermore, the body portion of portions may be cooled in a uniform manner via the liquid. Movement of users' body portions may operate to circulate liquid further equalizing temperatures throughout the liquid. After application of the therapeutic device for a time period, the body portion may be removed from the cool/cold.

Those skilled in the art will readily recognize, in light of and in accordance with the teachings of the present invention, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. For any method steps described in the present application that can be carried out on a computing machine, a typical computer system can, when appropriately configured or designed, serve as a computer system in which those aspects of the invention may be embodied. Thus, the present invention is not limited to any particular tangible means of implementation.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Having fully described at least one embodiment of the present invention, other equivalent or alternative methods therapeutic devices according to the present invention will be apparent to those skilled in the art. The invention has been described above by way of illustration, and the specific embodiments disclosed are not intended to limit the invention to the particular forms disclosed. For example, the particular implementation of the cooling devices may vary depending upon the particular size of the body portion being treated. The cooling devices described in the foregoing were directed primarily to implementations associated with athletic activities and events; however, similar techniques associated with non-athletic activities and events are contemplated as within the scope of the present invention. The invention is thus to cover all modifications, equivalents, and alternatives falling within the spirit and scope of the following claims.

Claim elements and steps herein may have been numbered and/or lettered solely as an aid in readability and understanding. Any such numbering and lettering in itself is not intended to and should not be taken to indicate the ordering of elements and/or steps in the claims.

What is claimed is:

1. A method comprising the steps of:
   preparing a cooling device for use in a therapeutic cooling apparatus, the cooling device comprising a self-contained unit, the therapeutic cooling apparatus comprising a cavity being configured to accept at least a portion of a user's body part, a quantity of a liquid for surrounding the portion of the body part and an apparatus portion being configured to retain the cooling device, the apparatus portion further comprising at least one divider separating the apparatus portion from the cavity, the at least one divider being configured to be operable for transferring heat from the liquid to the cooling device;
   chilling the cooling device by placing the cooling device and the therapeutic cooling apparatus into a refrigeration device;
   placing the portion of the body part into the cavity; and
   filling the cavity with the liquid to surround the portion of the body part enabling a heat transfer from the portion of the body part to the liquid and a heat transfer from the liquid through the divider to the cooling device to cool the user.

2. The method as recited in claim 1, further comprising the step of inserting the cooling device into the apparatus portion of the therapeutic cooling apparatus.

3. The method as recited in claim 1, further comprising the step of partially filling the cavity with the liquid prior to placing the portion of the body part into the cavity.

4. The method as recited in claim 1, in which said chilling comprises freezing the cooling device.

5. The method as recited in claim 1, in which said preparing comprises filling the cooling device with a cooling device liquid.

6. The method as recited in claim 5, in which said preparing further comprises sealing the cooling device liquid in the cooling device.

7. The method as recited in claim 1, in which said placing comprises placing at least a portion of the user's neck and head into the cavity.

\* \* \* \* \*